United States Patent
Dai et al.

(10) Patent No.: US 12,019,012 B2
(45) Date of Patent: Jun. 25, 2024

(54) MULTIVARIATE STATISTICAL CONTAMINATION PREDICTION USING MULTIPLE SENSORS OR DATA STREAMS

(71) Applicant: HALLIBURTON ENERGY SERVICES, INC., Houston, TX (US)

(72) Inventors: Bin Dai, Spring, TX (US); Christopher Michael Jones, Houston, TX (US); Anthony H. Van Zuilekom, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 17/979,359

(22) Filed: Nov. 2, 2022

(65) Prior Publication Data

US 2023/0053236 A1  Feb. 16, 2023

Related U.S. Application Data

(63) Continuation of application No. 16/473,964, filed as application No. PCT/US2018/016244 on Jan. 31, 2018, now Pat. No. 11,513,063.

(51) Int. Cl.
| | | |
|---|---|---|
| *E21B 47/12* | (2012.01) | |
| *E21B 47/06* | (2012.01) | |
| *E21B 49/08* | (2006.01) | |
| *G01N 21/31* | (2006.01) | |
| *G01N 21/59* | (2006.01) | |
| *G01N 21/94* | (2006.01) | |
| *G01N 33/28* | (2006.01) | |

(52) U.S. Cl.
CPC ............. *G01N 21/31* (2013.01); *E21B 47/06* (2013.01); *E21B 47/12* (2013.01); *E21B 49/0875* (2020.05); *G01N 21/5907* (2013.01); *G01N 21/94* (2013.01); *G01N 33/2823* (2013.01)

(58) Field of Classification Search
CPC ........ E21B 47/06; E21B 47/12; E21B 47/138; G01N 21/94; G01N 33/2823
See application file for complete search history.

(56) References Cited

U.S. PATENT DOCUMENTS

| | | | |
|---|---|---|---|
| 6,274,865 | B1 | 8/2001 | Schroer et al. |
| 7,305,306 | B2 | 12/2007 | Venkataramanan et al. |
| 7,711,488 | B2 | 5/2010 | Hsu et al. |
| 9,334,727 | B2 | 5/2016 | Jones et al. |
| 9,528,874 | B2 | 12/2016 | Larter et al. |
| 2006/0139646 | A1 | 6/2006 | DiFoggio |

(Continued)

OTHER PUBLICATIONS

International Search Report and Written Opinion; PCT Application No. PCT/US2018/016244; mailed May 9, 2018.

*Primary Examiner* — Catherine Loikith
(74) *Attorney, Agent, or Firm* — Polsinelli PC

(57) ABSTRACT

Systems and methods for performing a contamination estimation of a downhole sample comprising at least a formation fluid and/or a filtrate are provided. A plurality of downhole signals are obtained from the downhole sample and one or more of the signals are conditioned. At least two of the conditioned signals or downhole signals are fused into a multivariate dataset. From optical and density properties of the formation fluid and/or of the filtrate, a multivariate calculation is performed to generate concentration profiles of the formation fluid and the filtrate.

21 Claims, 10 Drawing Sheets

(56) References Cited

U.S. PATENT DOCUMENTS

| | | |
|---|---|---|
| 2013/0340518 A1 | 12/2013 | Jones et al. |
| 2014/0180591 A1 | 6/2014 | Hsu et al. |
| 2014/0208826 A1 | 7/2014 | Larter et al. |
| 2014/0278113 A1 | 9/2014 | Chok et al. |
| 2015/0226059 A1 | 8/2015 | Zuo et al. |
| 2015/0292324 A1 | 10/2015 | Jackson et al. |
| 2021/0201178 A1* | 7/2021 | Fanini .................... E21B 47/10 |

\* cited by examiner

MULTIVARIATE STATISTICAL CONTAMINATION PREDICTION USING MULTIPLE SENSORS OR DATA STREAMS

CROSS-REFERENCE TO RELATED APPLICATIONS

This application claims to the benefit of U.S. patent application Ser. No. 16/473,964 filed on Jun. 26, 2019, which is a national stage entry of PCT/US2018/016244 filed on Jan. 31, 2018, which claims benefit to U.S. Provisional Patent Application No. 62/453,422 filed on Feb. 1, 2017, the contents of each are hereby expressly incorporated by reference in their entirety.

TECHNICAL FIELD

The present technology pertains to calculating and predicting fluid contamination levels, and more specifically to a multivariate end-member fingerprint approach for calculating OBM filtrate contamination levels.

BACKGROUND

Downhole fluid sampling, also referred to as bottom-hole sampling, is a valuable tool in evaluating formations for the presence of hydrocarbons (or other fluids), and is often used to obtain a formation fluid sample from a well containing drilling mud or completion fluid. Advantageously, a formation fluid sample can be obtained downhole, as the name would imply, which avoids the complication or expense of having to produce the well to the surface in order to obtain the desired sample. However, there is typically very limited or no well cleanup performed prior to the sampling process, making it highly likely that the formation fluid sample will be contaminated by drilling mud filtrate. Various techniques have been proposed in order to detect and subsequently compensate for contamination with standard drilling mud filtrates.

When wells have been drilled with an oil based mud (OBM) filtrate, however, any contamination of the formation fluid sample is more difficult to detect and can be physically impossible to remove. Consequently, when performing downhole fluid sampling in wells containing OBM filtrate, an operator's goal is most typically to obtain a low contamination sample rather than a contamination free sample.

Conventional approaches to estimating OBM filtrate contamination of the formation fluid sample are generally known to heavily rely upon fluid density measurements, and more particularly, a high density contrast between the formation fluid and the OBM filtrate. Accordingly, these conventional techniques struggle in cases of low fluid density contrast, as the corresponding estimation error derived from the density measurement alone can be very large.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. The embodiments herein may be better understood by referring to the following description in conjunction with the accompanying drawings in which like reference numerals indicate analogous, identical, or functionally similar elements. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1A:
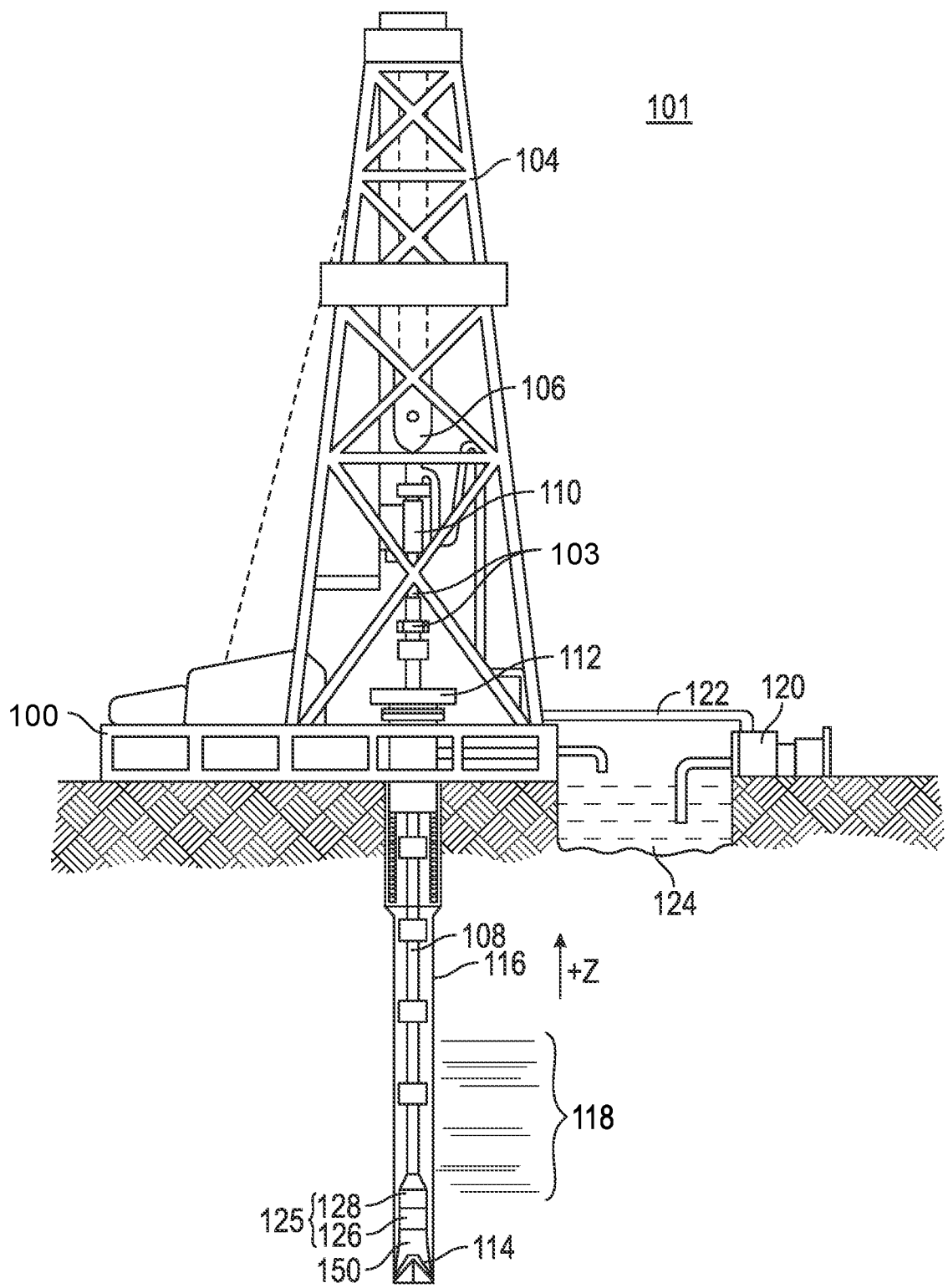
FIG. 1A illustrates a schematic diagram of a wellbore environment, showing logging while drilling (LWD) operations.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

It should be understood at the outset that although illustrative implementations of one or more embodiments are illustrated below, the disclosed apparatus and methods may be implemented using any number of techniques. The disclosure should in no way be limited to the illustrative implementations, drawings, and techniques illustrated herein, but may be modified within the scope of the appended claims along with their full scope of equivalents.

The various characteristics described in more detail below, will be readily apparent with the aid of this disclosure upon reading the following detailed description, and by referring to the accompanying drawings.

Aspects of the disclosure pertain to techniques for accurately determining oil-based mud (OBM) filtrate contamination during the downhole fluid sampling process. During the cleanup process, a number of sensors, such as densitometers and optical sensors with multiple optical channels, may be run continuously to collect density measurements and optical data from a fluid running through the flowline in a formation tester tool, such as an RDT (reservoir description tool). Bubble point and fluid resistivity are often measured as well. A downhole sample (alternatively referred to herein as a 'downhole fluid sample' or a 'fluid sample') can include a formation fluid and a filtrate such as OBM. It is appreciated that the present disclosure is not limited exclusively to formation fluid, but can instead encompass various other fluid(s) of interest for sampling and/or analysis purposes, and likewise, that the filtrate can encompass various other wellbore fluids that might be employed downhole. The downhole sample can be collected during or after drilling operations, perforation operations, production operations, testing operations, and various other wellbore operations, without limitation to land environments and aquatic environments. For each operation type, the presently disclosed downhole sample contamination analysis can provide information used to guide existing and/or future operations. For example, a well might be drilled and perforated on the possibility that it might provide access to hydrocarbon reserves of a sufficient value or quality to justify the expense of their production. Rather than bearing the cost of producing the well to the surface in order to thereby analyze the formation fluid and determine whether or not further production is viable, and rather than taking a contaminated downhole sample and receiving highly uncertain formation fluid analysis results, the disclosed downhole sample contamination analysis can permit a more robust, accurate, and cost-effective analysis of the formation fluid as compared to these conventional solutions. Using the formation fluid analysis with a known higher accuracy, an operator can make an appropriate decision on how to continue operations, e.g. produce from the existing well, perform further fracturing on the existing well, perform further treatment operations on the existing well, analyze/produce from a different location in the existing well, drill new wells for further production from the formation, shut down the existing well and drill another test well, shut down the existing well and abandon the formation exploration project, etc.

A downhole sample can be obtained directly from a formation such that any further mixing of the formation fluid and the wellbore filtrate is minimized, either in general or as a consequence of performing the sampling operation. For example, a downhole testing apparatus can be positioned to engage with a perforation between the wellbore and the formation. A downhole sample can also be obtained from the wellbore, where the formation fluid and wellbore filtrate have been allowed to mix. For example, a downhole testing apparatus can be positioned in the vicinity of the perforation from which formation fluid is flowing into the wellbore and mixing with the wellbore filtrate. In some embodiments, a downhole sample can comprise a fluid volume that is collected and substantially enclosed or physically constrained, e.g. into a sample container or vessel, such that the sample is analyzed within its enclosure or the enclosure is transported away from the collection location for subsequent sample analysis. For example, the fluid volume of the downhole sample might be collected into an interior analysis chamber of a downhole sampling tool or the fluid volume might be transported up the drill string for analysis at the surface or some other remotely located system. In some embodiments, a downhole sample can comprise a fluid volume that is not substantially enclosed or physically constrained, such that the sample is effectively analyzed in-situ and does not have to be removed or otherwise isolated from its surrounding environment.

The disclosed methods and techniques for determining OBM and other filtrate contamination levels during the downhole fluid sampling process relies in part upon data streams received from multiple sensors or sensor channels, such that OBM filtrate contamination levels can be determined regardless of whether or not an appreciable density contrast exists between the OBM filtrate and the formation fluid. Accurately determining the level of OBM filtrate contamination in a downhole sample has proven to be one of the biggest challenges in downhole fluid sampling and fluid sample quality determination. While cleanup techniques exist to remove OBM filtrate and any other muds or completion fluids from the well, these techniques are imperfect and some degree of contamination is often unavoidable.

Whereas conventional contamination analysis techniques require a relatively large density contrast in order to function, the present disclosure does not, and advantageously provides a robust and data-driven method to calculate OBM filtrate contamination profiles across various fluid density scenarios, including the low contrast scenario where conventional techniques fail. The disclosed method can leverage optical signals found in various optical spectral regions that provide greater contrast between OBM filtrate and formation fluid than conventional fluid density measurements. In some embodiments, the downhole fluid sample clean-up process is treated as a two end-member mixing problem, the two end members comprising formation fluid and OBM filtrate, which is solved using a multivariate curve resolution (MCR) algorithm. Rather than requiring an appreciable density contrast between OBM filtrate and formation fluid, the present disclosure instead fuses data from multiple optical channels and multiple sensors such that a robust and accurate determination of OBM contamination levels can be performed given any data that varies with fluid composition. In addition to OBM filtrate contamination levels, various other optical and physical properties of both pure formation fluid and OBM filtrate can be accurately determined according to embodiments of the present disclosure.

The disclosure turns now to FIG. 1A, which provides a schematic diagram of a wellbore environment 101 in which aspects of the present disclosure may be deployed. More particularly, depicted is a logging while drilling (LWD) operation, which is an example operation in which aspects of the present disclosure may be deployed. As depicted, wellbore environment 101 includes a drilling platform 100 equipped with a derrick 104 that supports a hoist 106 (alternatively known as a traveling block) for raising and lowering a drill string 108. Hoist 106 suspends a top drive 110 (alternatively known as a kelly) suitable for rotating the drill string 108 and lowering drill string 108 through a well head 112 (alternatively known as a rotary table). Connected to a lower end of drill string 108 is a drill bit 114. As drill bit 114 rotates, drill bit 114 creates a wellbore 116 that passes through various formations 118. One or more of these formations 118 may contain formation fluid that is of interest for analysis according to aspects of the present disclosure. A pump 120 circulates drilling fluid through a supply pipe 122 to top drive 110, down through an interior of drill string 108, through orifices in drill bit 114, back to the surface via an annulus around drill string 108, and into a retention pit 124. The drilling fluid transports cuttings from wellbore 116 into pit 124 and aids in maintaining the integrity of wellbore 116. Various materials can be used for drilling fluid, including oil-based fluids (such as OBM), various filtrates, and other water-based fluids. As mentioned previously, one or more of these drilling fluid materials may act to contaminate the formation fluid or more generally, the fluid of interest, in a downhole sampling process.

Logging tools 126 can be integrated into a bottom-hole assembly 125 near drill bit 114. A downhole tool 126 may take the form of a drill collar (i.e. a thick-walled tubular that provides weight and rigidity to aid the drilling process) or other arrangements known in the art. Further, downhole tool 126 may include acoustic (e.g., sonic, ultrasonic, etc.) and/or EM wave (e.g., visible light, infrared, etc.) logging tools and/or corresponding components, one or more of which may be integrated into bottom-hole assembly 125. Downhole tool 126 may further include one or more sensors (single or multi-channel) that can be configured to detect or otherwise measure optical and density properties of a downhole sample or other fluids. For example, the one or more sensors can include fiber optic sensors, densitometers, temperature sensors, pressure sensors, etc.

Each of logging tools 126 may include a plurality of tool components, spaced apart from each other, and communicatively coupled with one or more wires. Logging tools 126 may also include one or more computing devices 150 communicatively coupled with one or more of the plurality of tool components by one or more wires. A computing device 150 may be configured to control or monitor the performance of the tool, process logging data, and/or carry out the methods of the present disclosure.

In this fashion, as drill bit 114 extends wellbore 116 through subsurface formations 118, one or more of bottom-hole assembly 125 and logging tools 126 can collect measurements relating to various formation properties as well as the orientation of the tool and various other drilling conditions. A bottom-hole assembly 125 may also include a telemetry sub 128 to transfer measurement data to a surface receiver 103 and to receive commands from the surface. Mud pulse telemetry is one common telemetry technique for transferring tool measurements to surface receivers and receiving commands from the surface, but other telemetry techniques can also be used. In at least some instances, one or more of logging tools 126 may communicate with surface receiver 103 by a wire, provided by, for example, a slickline or a wired drillpipe. In other cases, one or more of logging tools 126 may communicate with surface receiver 103 by wireless signal transmission. In at least some cases, one or more of logging tools 126 may receive electrical power from a wire that extends to the surface, including wires extending through a wired drillpipe. In some embodiments, telemetry sub 128 can store logging data for later retrieval at the surface when the logging assembly is recovered. At the surface, surface receiver 103 can receive the uplink signal from the downhole telemetry sub 128 and can communicate the signal to a data acquisition module which can include one or more processors, storage mediums input devices, output devices, software and the like.

Figure 1B:
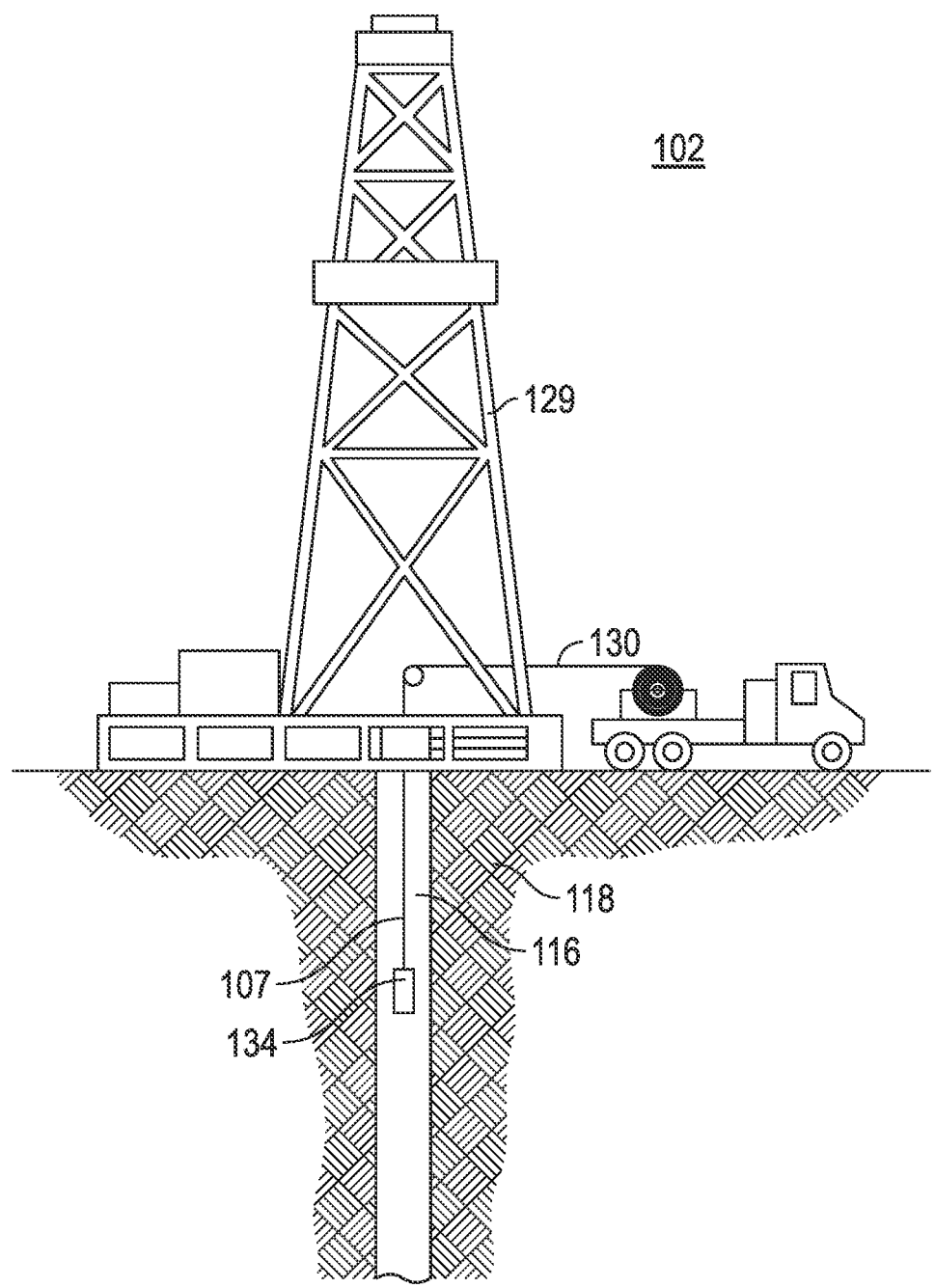
FIG. 1B is a schematic diagram of a wellbore environment, showing a downhole line detection operations.

At various times during the drilling process, drill string 108 may be removed from the borehole 116 as shown in FIG. 1B, which provides a schematic diagram of a wellbore operating environment 102 employing a wireline system. Once drill string 108 has been removed, logging operations can be conducted using a downhole tool 134 (i.e., a sensing instrument sonde) suspended by a conveyance 130. In some embodiments, downhole tool 134 includes one or more sensors (single or multi-channel) for detecting or otherwise measuring optical and density properties of a downhole sample. The one or more sensors can include fiber optic sensors, densitometers, temperature sensors, pressure sensors, etc. In one or more embodiments, the conveyance 130 can be a cable having conductors for transporting power to downhole tool 134 and transporting telemetry from the tool to the surface). Downhole tool 134 may have pads and/or centralizing springs to maintain the tool near the central axis of borehole 116 or to bias the tool towards the borehole wall as the tool is moved downhole or uphole. As a particular example, downhole tool 134 can include a Reservoir Description Tool (RDT™) Tool from Halliburton Energy Services, Inc., which provides a single deployment package for collecting formation pressure, fluid identification, and samples. An exemplary diagram of an RDT™ Tool can be seen in FIG. 3C, discussed below.

Remaining with FIG. 1B, it is noted that conveyance 130 can be anchored in drill rig 129 or anchored by other portable means such as a truck. In one or more embodiments, conveyance 130 of downhole tool 134 may be at least one of wires, conductive or non-conductive cable (e.g., wireline, slickline, fiber optic cable, etc.), as well as tubular conveyances such as coiled tubing, pipe string, downhole tractor, and other tubulars. The downhole tool 134 may have local power supply, such as batteries, a downhole generator, and the like. When employing non-conductive cable, coiled tubing, pipe string, or downhole tractor, communication may be supported, using, for example, wireless protocols (e.g., EM, acoustic, etc.) and/or measurements and logging data may be stored in local memory for subsequent retrieval. A logging facility (not shown) can be provided remotely or in-situ with respect to environment 102 and can include a computer system for collecting, storing, and/or processing the measurements gathered by logging tool 134.

In operation, subsurface formation 118 is traversed by borehole 116, which may be filled with drilling fluid or mud, such as a filtrate or OBM filtrate (not shown). Logging tool 134 is lowered into borehole 116 by a cable 107. As discussed, cable 107 connects to surface equipment (not shown) such as sheave wheels, derricks, winches, and the like, which operate to control descent/ascent of logging tool 134 through borehole 116. In addition, cable 107 may include electrical wiring and other electrical components that facilitates communication between logging tool 134 and the surface equipment. In addition, in also appreciated logging tool 134 may be configured for wireless communications. In this fashion, logging tool 134 may be equipped with various types of electronic sensors, transmitters, receivers, hardware, software, and/or additional interface circuitry for generating, transmitting, and detecting signals (e.g., sonic waves, etc.), storing information (e.g., log data), communicating with additional equipment (e.g., surface equipment, processors, memory, clocks, input/output circuitry, etc.), and the like. It is appreciated that various types of logging tools/devices may be used in conjunction with the techniques disclosed herein. Although FIGS. 1A and 1B depict specific borehole configurations, it should be understood that the present disclosure is equally well suited for use in wellbores having other orientations including vertical wellbores, horizontal wellbores, slanted wellbores, multilateral wellbores and the like. While FIGS. 1A and 1B depict an onshore operation, it should also be understood that the present disclosure is equally well suited for use in offshore operations. Moreover, the present disclosure is not limited to the environments depicted in FIGS. 1A and 1B, and can also be used, for example, in other well operations such as production tubing operations, jointed tubing operations, coiled tubing operations, combinations thereof, and the like.

Figure 1C:
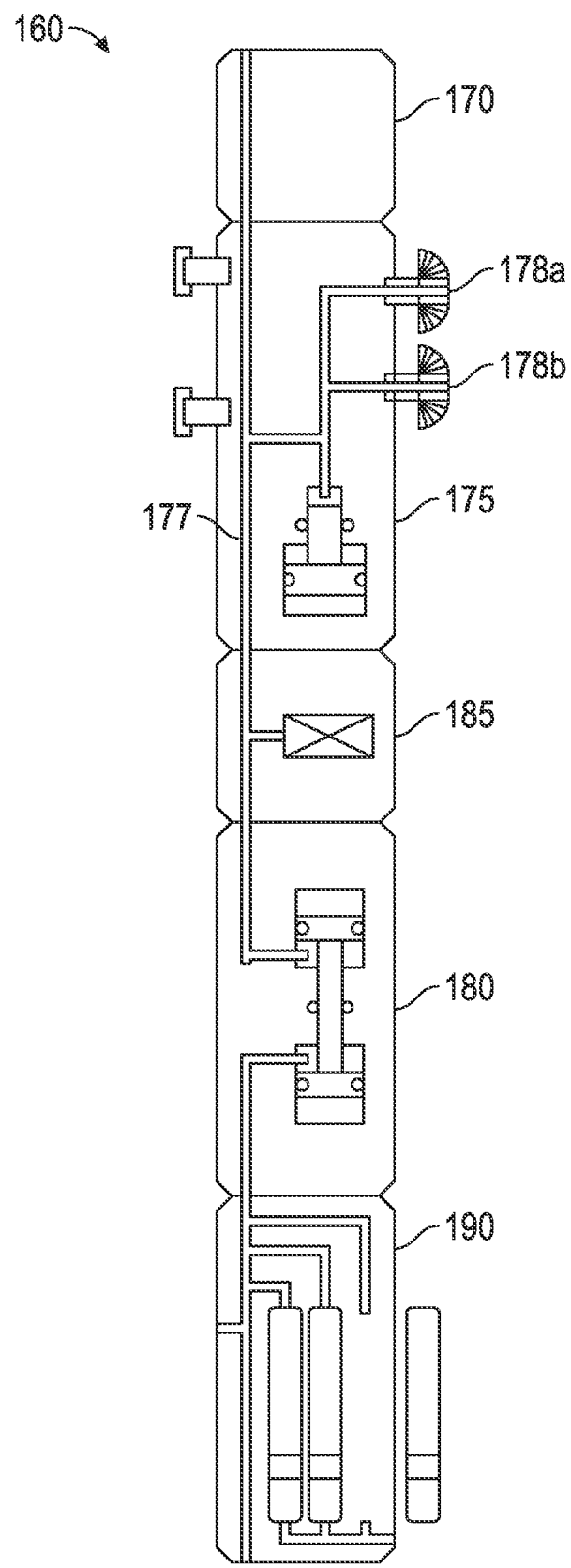
FIG. 1C is a schematic diagram of a modular downhole formation-testing tool, which can be used in downhole sampling operations.

FIG. 1C depicts a modular downhole formation testing tool 160 compatible with use in a downhole sampling process. In some embodiments, the formation testing tool 160 is a Reservoir Description Tool (RDT™) Tool from Halliburton Energy Services, Inc. RDT 160 is suitable for testing, retrieval and sampling along sections of a formation by means of contact with the surface of a borehole. A power and telemetry module 170 provides power to the various sections of RDT 160 and further provides telemetry and guidance information for control of RDT 160.

Probe module 175 comprises electrical and mechanical components that facilitate testing, sampling and retrieval of downhole fluid samples, i.e. of formation fluid(s). For example, probe 175 is provided with at least one elongated sealing pad to provide sealing contact with a surface of the borehole at a desired location, e.g. at a perforation between the borehole and a formation. Through one or more slits, fluid flow channels, or recesses in the sealing pad, fluids from the sealed-off part of the borehole or formation surface may be collected through the fluid path of two probes 178$a$, 178$b$ and their coupled flow line 177. In some embodiments, the slits in the sealing pad are elongated along the same elongation axis of the elongated sealing pad, and are generally applied along the longitudinal axis of the borehole. In some embodiments, downhole fluid sample collection can be actively forced by flow control module 180, which can comprise a double acting piston pump. Flow control module 180 may further accommodate strain-gauge pressure transducers that measure an inlet and outlet pump pressures and/or temperature sensors that measure inlet and outlet temperatures.

One or more setting rams (not shown on probe 175) can be located opposite probes 178$a$ and 178$b$. The setting rams can be laterally movable by actuators placed inside probe 175 to extend away from RDT 160. Probes 178$a$ and 178$b$ may have high-resolution temperature compensated strain gauge pressure transducers (not shown) that can be isolated with shut-in valves to monitor the probe pressure and temperature independently. When resistance, optical, densitometer, or other types of sensors are included, they may be provided near probes 178$a$ and 178$b$ in order to monitor the downhole sample fluid properties immediately after the sample enters either probe.

Flow line 177 additionally couples to fluid testing section 185, which contains a fluid testing device and/or one or more sensors, including optical sensors, densitometers, temperature sensors, pressure sensors, etc. for analysis or measurement and characterization of downhole fluid samples collected by RDT 160. The downhole fluid samples can be stored in sample collection module 190, which contains various sized collection chambers. In this manner, RDT 160 can obtain the measurements of the downhole fluid sample that are used as input to the analysis of the present disclosure. In some embodiments, the contamination analysis of the present disclosure can be performed on-board RDT 160, for example via fluid testing section 185, although it is appreciated that the analysis may be performed at other apparatuses and/or locations without departing from the scope of the disclosure.

Figure 2A:
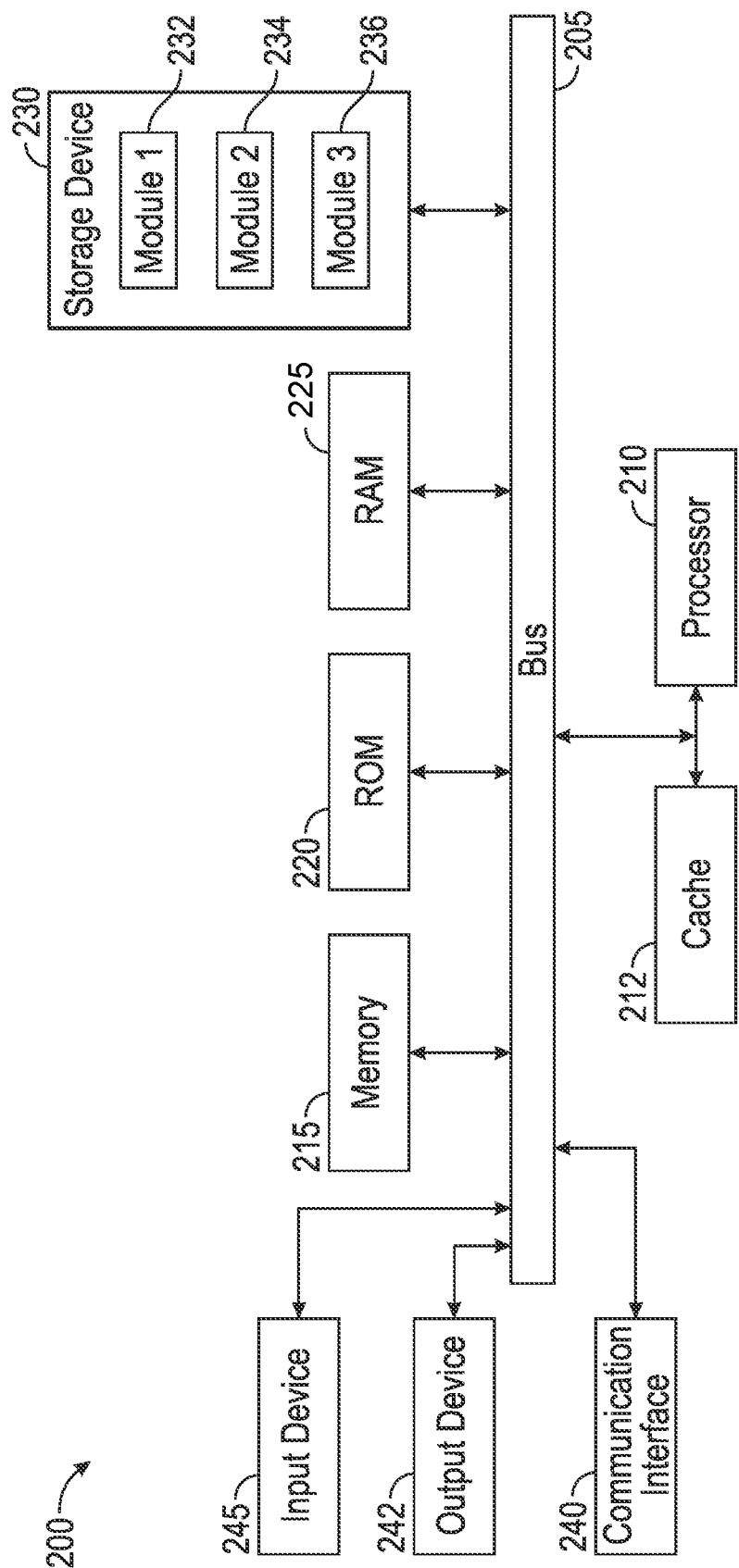
FIGS. 2A and 2B are schematic diagrams of example system embodiments.
Figure 2B:
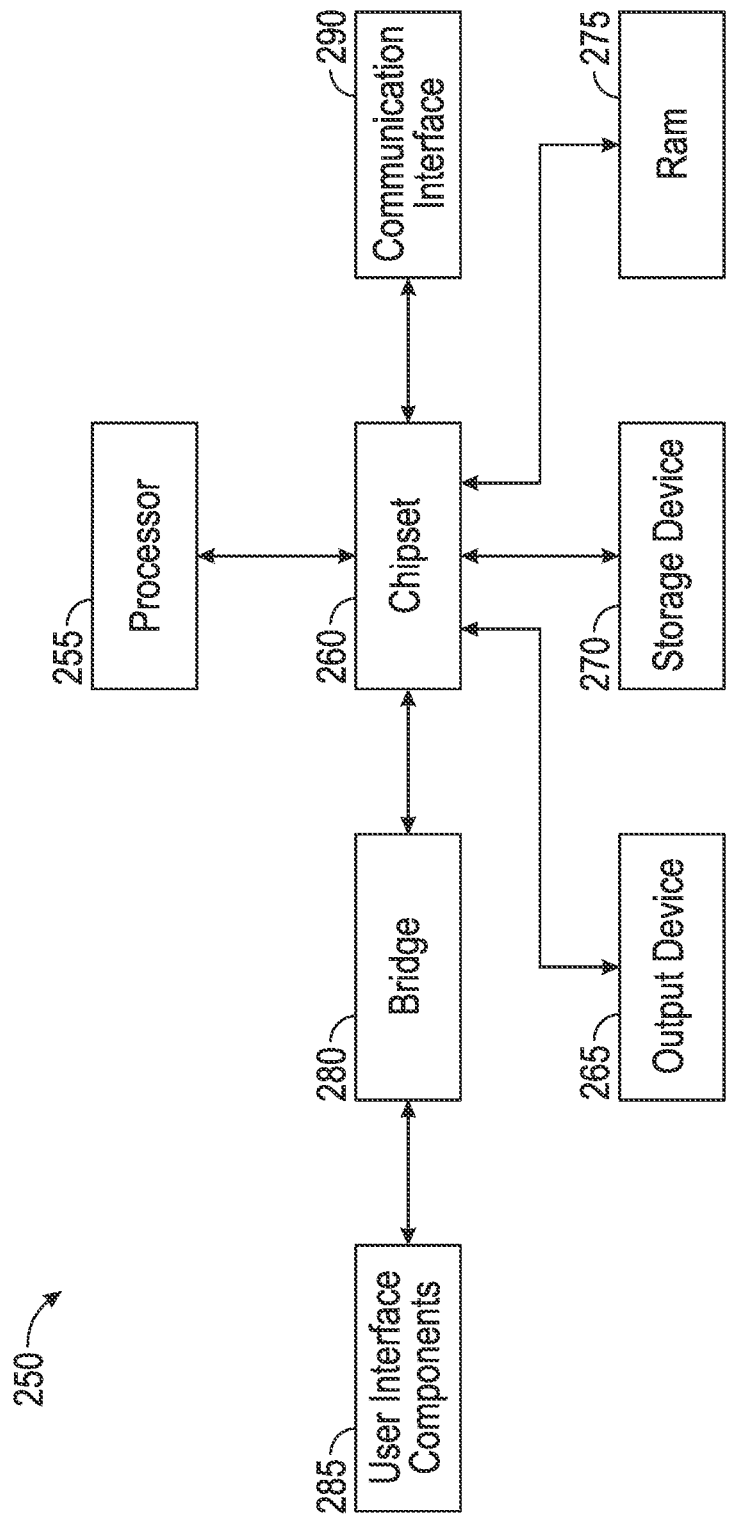

FIGS. 2A and 2B illustrate exemplary computing systems for use with example tools and systems (e.g., downhole tool 26, downhole tool 34, surface equipment, and the like). The more appropriate embodiment will be apparent to those of ordinary skill in the art when practicing the present technology. Persons of ordinary skill in the art will also readily appreciate that other system embodiments are possible.

FIG. 2A illustrates system architecture 200 wherein the components of the system are in electrical communication with each other using a bus 205. System architecture 200 can include a processing unit (CPU or processor) 210 and a system bus 205 that couples various system components including the system memory 215, such as read only memory (ROM) 220 and random access memory (RAM) 225, to the processor 210. System architecture 200 can include a cache of high-speed memory connected directly with, in close proximity to, or integrated as part of the processor 210. System architecture 200 can copy data from the memory 215 and/or the storage device 230 to the cache 212 for quick access by the processor 210. In this way, the cache can provide a performance boost that avoids processor 210 delays while waiting for data. These and other modules can control or be configured to control the processor 210 to perform various actions. Other system memory 215 may be available for use as well. The memory 215 can include multiple different types of memory with different performance characteristics. The processor 210 can include any general purpose processor and a hardware module or software module, such as module 1 (232), module 2 (234), and module 3 (236) stored in storage device 230, configured to control the processor 210 as well as a special-purpose processor where software instructions are incorporated into the actual processor design. The processor 210 may essentially be a completely self-contained computing system, containing multiple cores or processors, a bus, memory controller, cache, etc. A multi-core processor may be symmetric or asymmetric.

To enable user interaction with the computing system architecture 200, an input device 245 can represent any number of input mechanisms, such as a microphone for speech, a touch-sensitive screen for gesture or graphical input, keyboard, mouse, motion input, speech and so forth. An output device 242 can also be one or more of a number of output mechanisms. In some instances, multimodal systems can enable a user to provide multiple types of input to communicate with the computing system architecture 200. The communications interface 240 can generally govern and manage the user input and system output. There is no restriction on operating on any particular hardware arrangement and therefore the basic features here may easily be substituted for improved hardware or firmware arrangements as they are developed.

Storage device 230 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 225, read only memory (ROM) 220, and hybrids thereof.

The storage device 230 can include software modules 232, 234, 236 for controlling the processor 210. Other hardware or software modules are contemplated. The storage device 230 can be connected to the system bus 205. In one aspect, a hardware module that performs a particular function can include the software component stored in a computer-readable medium in connection with the necessary hardware components, such as the processor 210, bus 205, output device 242, and so forth, to carry out the function.

FIG. 2B illustrates an example computer system 250 having a chipset architecture that can be used in executing the described method and generating and displaying a graphical user interface (GUI). Computer system 250 can be computer hardware, software, and firmware that can be used to implement the disclosed technology. System 250 can include a processor 255, representative of any number of physically and/or logically distinct resources capable of executing software, firmware, and hardware configured to perform identified computations. Processor 255 can communicate with a chipset 260 that can control input to and output from processor 255. Chipset 260 can output information to output device 265, such as a display, and can read and write information to storage device 270, which can include magnetic media, and solid state media. Chipset 260 can also read data from and write data to storage 275 (e.g., RAM). A bridge 280 for interfacing with a variety of user interface components 285 can be provided for interfacing with chipset 260. Such user interface components 285 can include a keyboard, a microphone, touch detection and processing circuitry, a pointing device, such as a mouse, and so on. In general, inputs to system 250 can come from any of a variety of sources, machine generated and/or human generated.

Chipset 260 can also interface with one or more communication interfaces 290 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 255 analyzing data stored in storage 270 or 275. Further, the machine can receive inputs from a user via user interface components 285 and execute appropriate functions, such as browsing functions by interpreting these inputs using processor 255.

It can be appreciated that systems 200 and 250 can have more than one processor 210 or be part of a group or cluster of computing devices networked together to provide greater processing capability.

Figure 3:
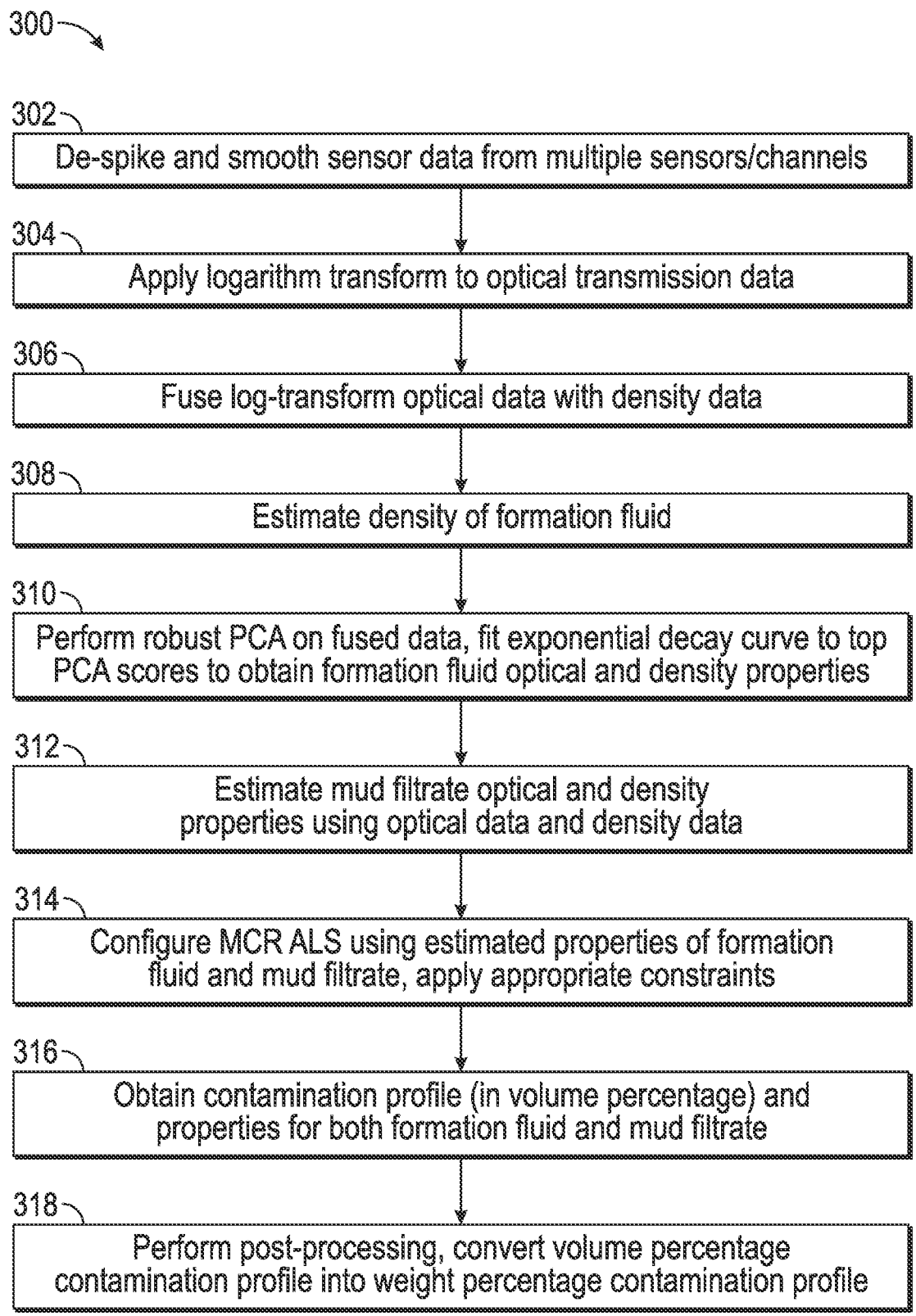
FIG. 3 is a flowchart of an exemplary method of the disclosure.

FIG. 3 is an example flow chart 300 of a procedure for the contamination estimation method of the present disclosure. Provided below is a brief summary of the individual components of flow chart 300. Subsequent to the brief summary, the disclosure will turn to a more detailed and in-depth exploration of each individual component of flow chart 300.

As shown, in step 302 signals are first received from multiple sensors and are de-spiked and smoothed in accordance with various data conditioning techniques known in the art. In step 304, optical transmission data is subjected to a logarithm transform and in step 306, the transformed data is fused with a density signal from step 302 in order to create a fused multivariate data set. In step 308, the density of formation fluid is estimated, for example via exponential decay curve. The method then proceeds to step 310, wherein a robust Principal Component Analysis (PCA) is performed on the fused multivariate data set of step 306. An exponential decay curve fitting is then performed on the top PCA scores in order to obtain optical and density properties of the formation fluid. In step 312, the optical and density properties of the formation fluid are used to estimate optical and density properties of the mud filtrate or OBM filtrate. The method then performs multivariate curve resolution (MCR) in step 314, using the optical and density properties of both the formation fluid (from step 310) and the OBM filtrate (from step 314). From the output of the MCR, a resolved contamination profile and properties of the two end-members are extracted in step 316. In some embodiments, the contamination profile is measured in a volume percentage and the two end-members are given by the formation fluid and the OBM filtrate. Finally, in step 318, the volume percentage contamination profile from step 316 is converted into a weight percentage contamination profile for the OBM filtrate. While the individual steps are presented in flowchart 300 in a certain consecutive order, this order is not intended to be limited and is provided by way of example. For example, although steps 308 and 310 are depicted in consecutive fashion, it is appreciated that they may be performed simultaneously or step 310 may otherwise begin prior to the completion of step 308, as the PCA analysis of step 310 operates on the multivariate fused data set of step 306 and does not depend on the output of step 308. Further details regarding these individual steps are provided below. While specific reference is made to density signals and optical signals, it is appreciated that other combinations of signals may be utilized and the below example is not intended to be limiting.

Step 302—De-Spike and Smooth Signal Data

The method begins by receiving a plurality of substantially real-time signals, which can include raw measured signals, calculated signals, or both. The plurality of real-time signals may be different, or there may be multiple instances of the same signal or signal type. In one example, in the context of a downhole sample cleanup process, a number of sensors, including densitometers and optical sensors with multiple optical channels, can be run continuously to collect density and optical signals. In some embodiments, sensors can further be provided to measure bubble point and resistivity of one or more fluids. It is appreciated that, rather than receiving each signal of the plurality of substantially real-time signals from a discrete sensor or sensing apparatus, multiple signals may be received from a corresponding multiplicity of channels of a single sensor or sensing apparatus. In other words, the number of received signals need not exactly equal the number of sensors or sensing apparatuses provided, although such an occurrence is within the scope of the present disclosure.

Regardless of the particular correspondence between the number of signals and the number of sensors, it is further contemplated that one or more of the plurality of substantially real-time signals can be collected from a downhole environment, such as environments 101 and 102 of FIGS. 1A and 1B respectively, via logging tools 126 and 134, or otherwise by being placed downhole in order to obtain the requisite data in a suitable manner. In some embodiments, the optical signals may be transmitted for storage and/or analysis using some combination of visible and near/mid-infrared light, although other wavelengths and transmission techniques may be utilized.

Figure 4:
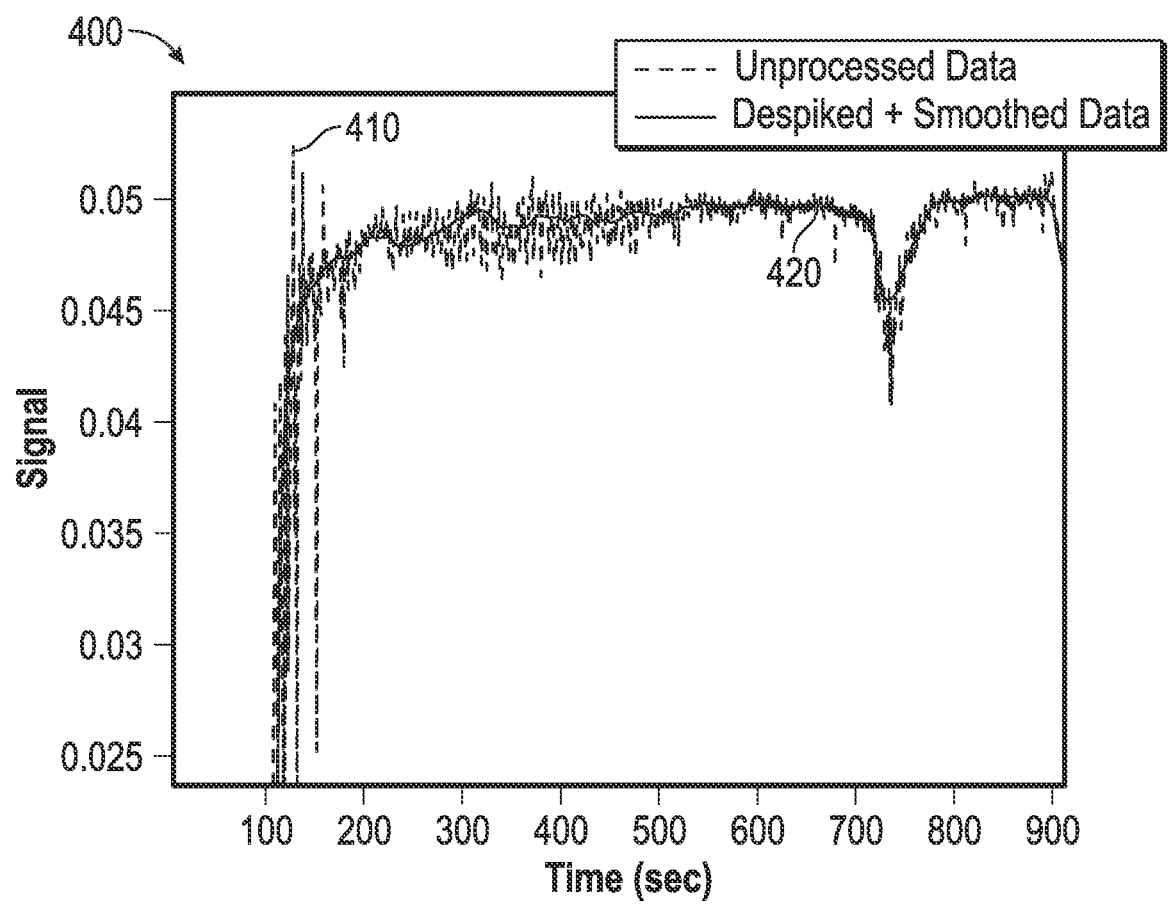
FIG. 4 is an exemplary signal before and after undergoing conditioning.

Once obtained, the plurality of substantially real-time signals may be subjected to some combination of filtering and conditioning. For example, the substantially real-time signals received from both optical sensors and densitometers are often noisy and contain signal spikes at various points throughout the entire downhole cleanup process. Accordingly, it is often desirable to de-spike and smooth any raw measured signals in order to obtain more accurate and robust results in the OBM contamination profile. The results of one such exemplary data conditioning process as applied to an optical transmission measurement signal are depicted in FIG. 4, which is a graph 400 containing a raw measured optical transmission signal 410 (labeled as 'unprocessed data' and depicted with a thinner line) and a resulting conditioned optical transmission signal 420 (labeled as 'de-spiked+smoothed data' and depicted with a thicker line). As can be seen in graph 400, the signal conditioning process results in conditioned optical transmission signal 420 which contains a substantially reduced amount of both noise and jitter as compared to the raw measured optical transmission signal 410. In some embodiments, the depicted data conditioning process can be applied to each signal of the plurality of substantially real-time signals, e.g. a raw measured optical signal would result in a conditioned optical signal, a raw measured density signal would result in a conditioned density signal, etc. Because these signals are time varying, it is contemplated that data conditioning can also be performed in substantially real-time as each signal is received. In some embodiments, the received signals can be processed in blocks or time steps, wherein the received signal is stored in a buffer until the desired block or time step length has been received (e.g. 10 seconds of data), at which point in time the signal conditioning can be applied to the stored signal corresponding to the desired block or time step length. While the precise manner in which noise and jitter present themselves may vary based on the particular type of raw measured signal, it is understood that the general process of signal conditioning can be applied to any noisy signal, regardless of its specific origin or measurement frequency.

While specific reference has thus far been made to optical sensors and densitometers, and their resultant optical and density signals both raw and processed, it is appreciated that various other combinations of sensors and sensor signals can be utilized without departing from the present disclosure. Such sensors and sensor signals include, but are not limited to capacitance, compressibility, temperature, and pressure. In some embodiments, calculated signals based on a measured sensor signal can likewise be employed. In some embodiments, a plurality of substantially real-time signals can be received and each signal analyzed in order to determine whether or not the signal varies with a downhole fluid composition. If it is determined that the signal does not vary with a downhole fluid composition, then the signal can be de-weighted or discarded entirely such that only signals that are determined to vary (or likely vary) with a downhole fluid composition are subjected to the data conditioning process and subsequently transmitted for further processing and analysis.

Step 304—Logarithm Transform of Smoothed Optical Transmission Data

Next, one or more optical signals that were de-spiked, smoothed, or otherwise conditioned in step 302 are transformed into absorbance signals. This transformation acts to ensure the linearity of subsequent optical signal mixing, and accordingly, is not necessarily applied to density signals or other non-optical signals that might be collected and/or processed in step 302. In some embodiments, a logarithm transformed is utilized to transform the optical transmission measurement signals to absorbance signals, although it is appreciated that various other techniques and data processing algorithms may be applied in order to effect the requisite transformation into absorbance signals. In some instances, the optical channel associated with a sensor or sensor channel may output signals that already are known to exhibit linearity in optical mixing, in which case step 304 is not strictly required. For example, the optical channel may include an integrated computational element (ICE) filter, which thereby causes the filtered optical channel to output ICE transformed signals which already exhibit linearity in optical mixing. Such characterizing information of the sensor or sensor channel can be saved or stored, for in example, in a centralized database underlying the presently disclosed signal processing systems and techniques.

Step 306—Fusion of Transformed Optical Data and Smoothed Density Data

Figure 5:
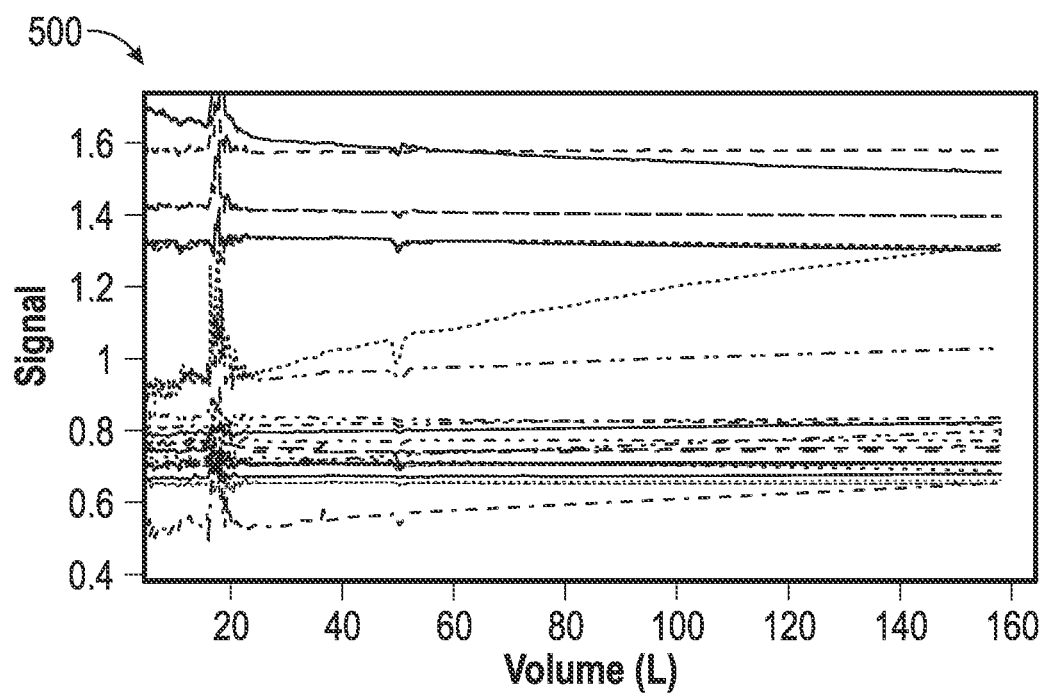
FIG. 5 is an exemplary fused multivariate dataset.

Next, the transformed optical signals from step 304 (i.e. what are now absorbance signals) are fused with one or more density signals that were de-spiked, smoothed, or otherwise conditioned in step 302. The fusion of this density data and the transformed optical signals yields a fused multivariate dataset. FIG. 5 illustrates one such exemplary fused multivariate data set 500 derived from multiple optical channel signals and multiple density signals. Here, the vertical axis indicates signal strength, which may be normalized, while the horizontal axis corresponds to the pump volume (in liters) of the downhole sampling that is undergoing a contamination analysis according to the present disclosure. Although indicated as preceding step 308, in some embodiments step 306 and 308 may be performed concurrently, or step 308 may be performed prior to step 306.

Step 308—Estimate Density of Formation Fluid

Figure 6:
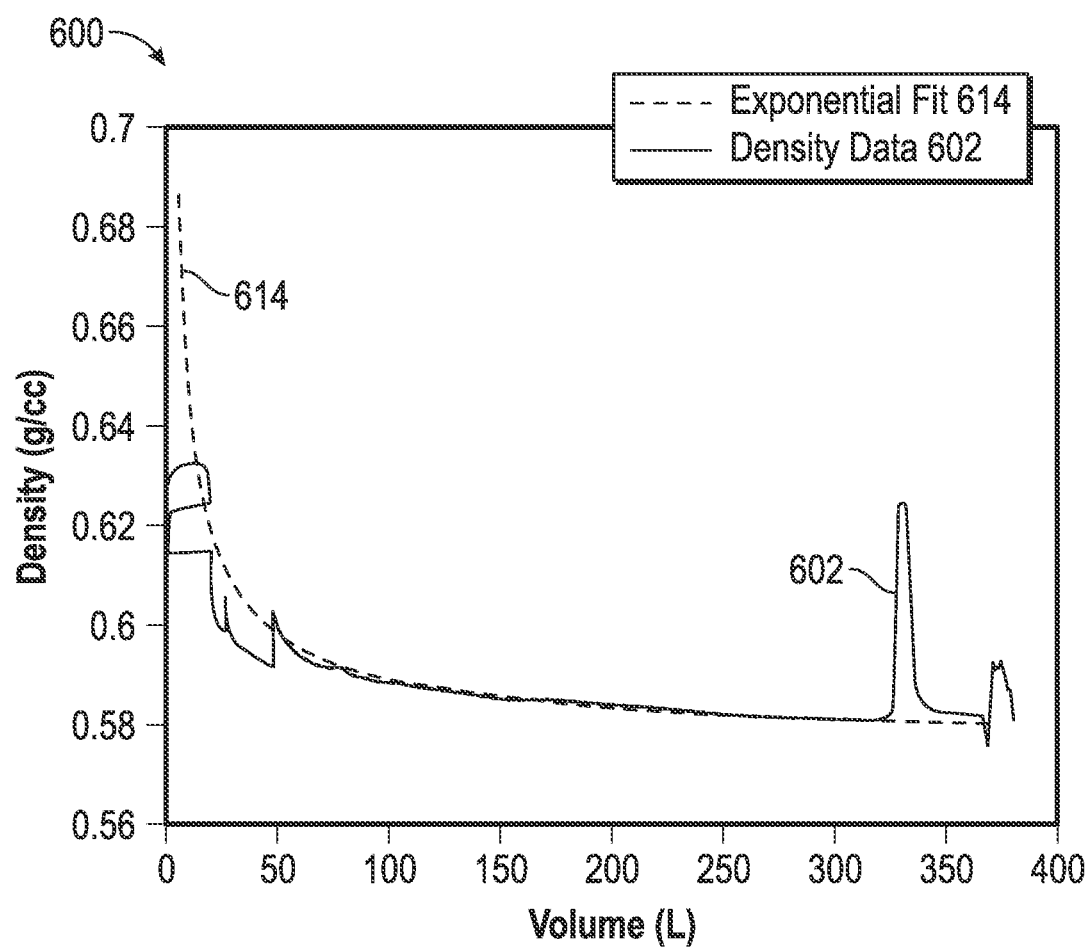
FIG. 6 is an exemplary exponential decay fitting of density data.

An initial estimate of the density of formation fluid will be used as an input to the presently disclosed MCR algorithm (discussed in further detail in steps 314 and 316). In some embodiments, this estimate can be obtained by fitting an exponential decay curve to density data, e.g. the smoothed density data of step 302, raw density data obtained from a sensor or sensor channel, etc. FIG. 6 illustrates an example graph 600 containing density data 602 and an exponential decay curve 614 fit to the density data 602. Exponential decay curve 614 can be calculated in a variety of ways in order to obtain a best-fit against the density data 602, according to one or more curve fitting techniques as are known in the art. For purposes of discussion, consider a best-fit exponential decay curve of the following form:

$$\rho(vol) = \rho_F + \beta \cdot vol^{-2/3} \qquad (1)$$

where the best-fit exponential decay curve $\rho(vol)$ is a modeled density curve of OBM filtrate as a function of pump volume vol and $\beta$ is a calculated exponential decay parameter. The intercept term $\rho_F$ can, notably, be estimated as the density of one end member (i.e. formation fluid), because $\rho_F$ is obtained by taking the limit of $\rho(vol)$ as vol goes to infinity, as is evident from Equation (1). Thus, the intercept term $\rho_F$ is alternately referred to herein as the estimated formation fluid density.

In some embodiments, one or more end members, the formation fluid, the OBM filtrate, etc. can be characterized a priori, via, for example, a proxy sample, a library database, lab experimentation, or directly at a well site, in which case it is not strictly necessary to perform the above disclosed density estimation. In some embodiments, an end member guess (such as the formation fluid density) can be calculated based on a concentration profile which estimates a relative concentration magnitude for each of the two end members (i.e. formation fluid and OBM filtrate in this example).

In general, it is desirable to avoid conditioning or initializing the multivariate end-member fingerprint method of the present disclosure with a density estimate that is too far removed from reality. In other words, an exact estimation is not required for the method to work, but a reasonable estimate is. Accordingly, it is appreciated that the present disclosure is not limited solely to the best-fit estimation or a priori estimations described above, and that additional techniques can be employed in order to generate a reasonable end member estimation or characterization.

Step 310—Estimate Formation Fluid Optical and Density Properties

Using the fused multivariate dataset obtained in step 306 (e.g. multivariate dataset 500 of FIG. 5) obtained, a principal component analysis (PCA) is performed. The PCA begins with a decomposition of the fused multivariate dataset D as follows:

$$D = S \cdot L + E \qquad (2)$$

where S represents the PCA scores, L represents the PCA loadings (i.e. the principal components), and E is a residual error value. The number of principal components can vary based on the particular fused multivariate dataset being analyzed, but in general is less than or equal to the number of original variables found in the fused multivariate dataset D. In some embodiments, only the top two principal components and their associated PCA scores, e.g. PC1 and PC2, are kept as the PCA scores S. In some embodiments, only the top principal component and its associated PCA score, e.g. PC1, might be utilized as the PCA scores S.

Figure 7:
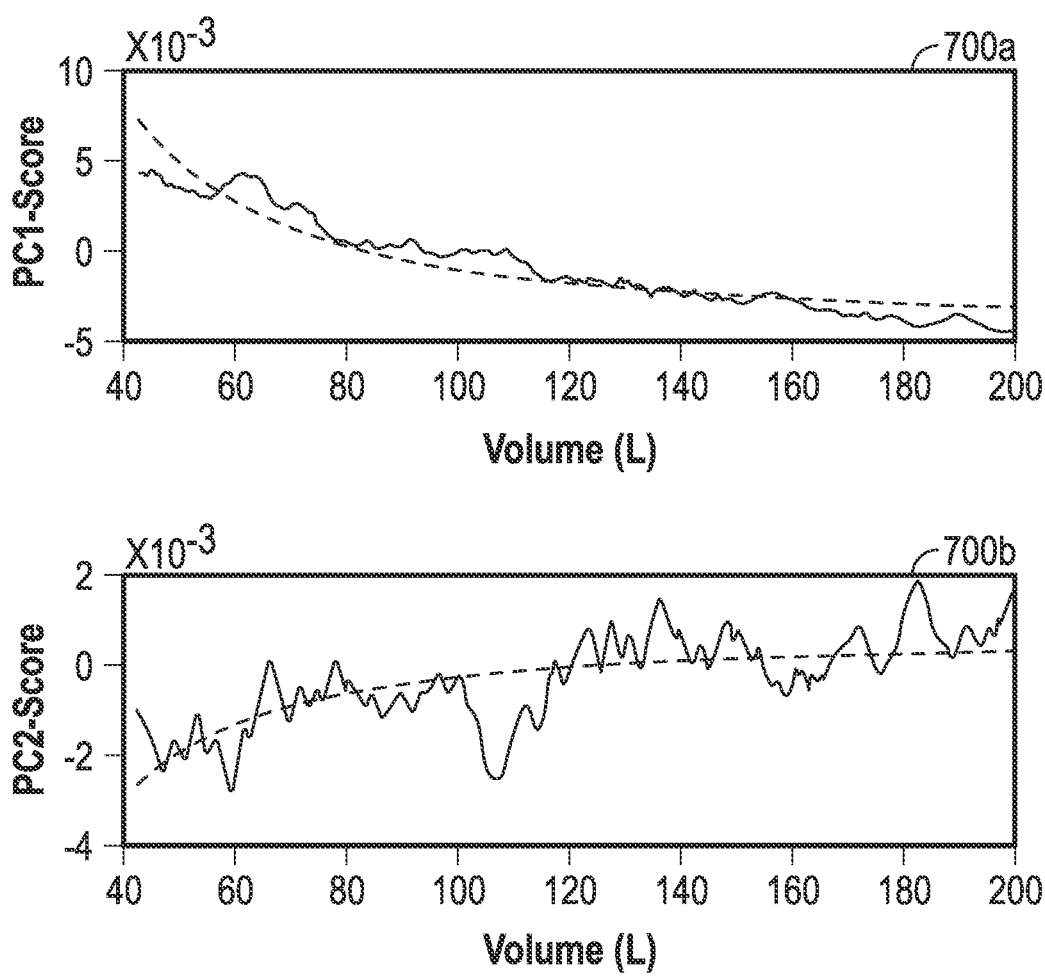
FIG. 7 is an exemplary exponential curve fitting to PCA scores.

An exponential decay curve is then fit to the PCA scores S yielded by Equation (2), as described above. FIG. 7 illustrates one such example exponential decay curve fitting, where graph 700a depicts an exponential decay curve 704 fit to the PC1 scores of the first principal component and graph 700b depicts an exponential decay curve 714 fit to the PC2 scores of the second principal component. In the context of the present disclosure, consider once again an exponential decay curve fitting for the PCA scores which takes the following form:

$$S = S_F + \beta(\text{vol})^{-2/3} \quad (3)$$

where β is a best-fit exponential decay parameter for the PCA scores S and vol is pump volume. As was discussed in step 308, the intercept term $S_F$ can be taken as an estimate of the PCA score(s) for formation fluid, because $S_F$ is calculated as vol goes to infinity. It is noted that, although Equations (1) and (3) are similar it is not necessarily the case that they share the same decay parameter, as it is understood that any given decay parameter β is specific to the given input data set against which it is calculated. Further still, it is noted that steps 306 and 308 need not be performed in successive order and may instead be performed concurrently, given that step 308 operates upon the fused multivariate dataset of step 304 and does not depend on step 306 as input.

From $S_F$, the formation fluid optical and density properties $\hat{D}_F$ can be extrapolated by projecting the estimated formation fluid PCA scores $S_F$ into the PCA loading space L from the PCA decomposition of Equation (2):

$$\hat{D}_F = S_F \cdot L \quad (4)$$

These extrapolated formation fluid optical and density properties $\hat{D}_F$ will later be used in steps 314 and 316 as an end member input to the presently disclosed MCR algorithm.

Step 312—Estimate OBM Filtrate Optical and Density Properties

Two different scenarios are contemplated in which the OBM filtrate optical and density properties must be estimated. These two scenarios are treated in turn below. In the first scenario, a strong fluid density contrast exists between the OBM filtrate density and the formation fluid density. In the second scenario, little fluid density contrast exists between the OBM filtrate density and the formation fluid density.

Scenario One: Strong Fluid Density Contrast

When there is a strong fluid density contrast between OBM filtrate and formation fluid, upper and lower boundaries of OBM filtrate density, $\rho_{M,U}$ and $\rho_{M,L}$ respectively, can be estimated based on one or more of the type of OBM filtrate used, the formation pressure, and the formation temperature. For example, OBM filtrate density may be estimated or characterized to be between a lower limit of $\rho_{M,L}=0.78$ g/cc (grams per cubic centimeter) and an upper limit of $\rho_{M,U}=0.86$ g/cc, these limits based on the known material properties and performance characteristics of the specific OBM filtrate being used and further based on the knowledge that the OBM filtrate experiences a pressure of 3 ksi (ksi=thousands of pounds per square inch) and a temperature of 195 degrees Fahrenheit in the wellbore.

Based on these estimated OBM filtrate density boundaries, the estimated formation fluid density $\rho_F$ from step 308, and real-time fluid density measurement data ρ (from an RDT tool, for example), it is possible to calculate a lower boundary $\gamma_L$ and an upper boundary $\gamma_U$ of the OBM filtrate contamination level at any time point during the sample cleaning up process. These two boundaries on the OBM filtrate contamination level are given as follows:

$$\gamma_L = (\rho - \rho_F)/(\rho_{M,U} - \rho_F) \quad (5)$$

$$\gamma_U = (\rho - \rho_F)/(\rho_{M,L} - \rho_F) \quad (6)$$

where ρ is the real-time fluid density measurement, $\rho_F$ is the estimated formation fluid density from step 308, $\rho_{M,U}$ is the upper boundary of OBM filtrate density, and $\rho_{M,L}$ is the lower boundary of OBM filtrate density.

Once these two boundaries of OBM filtrate contamination level are determined, estimated OBM filtrate optical and density properties $D_M$ can be obtained as follows:

$$D_M = (D - (1-\gamma)\hat{D}_F)/\gamma \quad (7)$$

where D is a real-time optical properties measurement obtained downhole by the RDT tool, γ is the density-based contamination level between $\gamma_L$ and $\gamma_U$, and $\hat{D}_F$ is the extrapolated formation fluid optical and density properties from Equation (4) of step 310. Note that the OBM filtrate optical and density properties $D_M$ are estimated based on real-time measurements whereas the formation fluid optical and density properties $\hat{D}_F$ are extrapolated based on a projection of PCA scores into the loading space L—in this first scenario of high fluid density contrast between the OBM filtrate and the formation fluid, only one PCA score extrapolation/projection is performed.

Scenario Two: Little to No Fluid Density Contrast

In the second scenario, where there is little to no fluid density contrast present between the OBM filtrate and the formation fluid (or the fluid density measurement ρ is not reliable), it can be difficult or impossible to obtain estimates for the OBM filtrate density boundaries $\rho_{M,U}$ and $\rho_{M,L}$, which are inputs to Equations (5) and (6), respectively. Without the OBM filtrate density boundaries, it is therefore difficult or impossible to perform the above analysis of Equations (5), (6) and (7) in order to obtain the estimated OBM filtrate optical and density properties $D_M$. In lieu of this analysis, the OBM filtrate optical and density properties can be determined using PCA scores in much the same manner in which the formation fluid optical and density properties were extrapolated using PCA scores in step 310.

Figure 8:
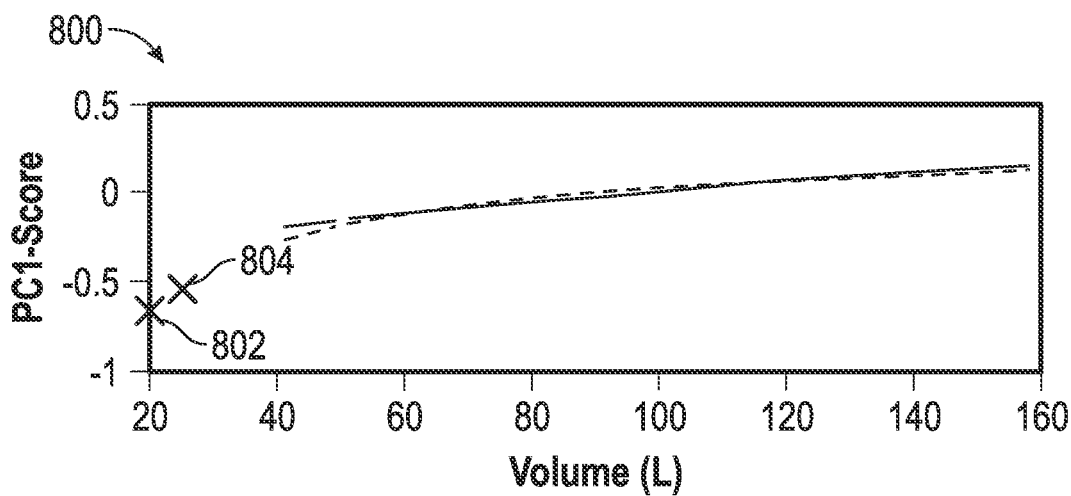
FIG. 8 is an exemplary extrapolation of a PCA score fitting curve to obtain PCA score boundaries.

In particular, one or more of the best-fit exponential decay curves obtained in step 310 can be extrapolated to one or more early pump-out times, i.e, times at which there has been only a small pump-out volume from the well cleanup process. Graph 800 of FIG. 8 depicts a first extrapolated point 802 (corresponding to a pump-out volume of 20 liters) and a second extrapolated point 804 (corresponding to a pump-out volume of 25 liters). These two extrapolated points 802 and 804 fall during what can be referred to as an 'early pump-out window', which in graph 800 runs from approximately 0-40 L on the horizontal axis. During this early pump-out window, and thus at extrapolated points 802 and 804, the concentration of OBM filtrate in the well is near its peak and the OBM filtrate properties dominate, relatively speaking. As such, PCA scores extrapolated from this early pump-out window can be used to determine OBM filtrate optical and density properties in the absence of a strong fluid density contrast between OBM filtrate and formation fluid.

From these two extrapolated points 802 and 804, PCA scores $S_M$ for the OBM filtrate can be estimated. In some embodiments, the extrapolated points 802 and 804 might be used to determine upper and lower boundaries for the OBM filtrate PCA scores such that the PCA scores $S_M$ can be determined more efficiently in view of the upper and lower boundaries. In some embodiments, $S_M$ might comprise the upper and lower boundaries themselves rather than comprising one or more PCA scores falling within these boundaries.

Independent of how $S_M$ is configured, $S_M$ is then projected into the PCA loading space L that was determined from the PCA decomposition of Equation (2), where the projection takes the following form:

$$\tilde{D}_M = S_M \cdot L \qquad (8)$$

$\tilde{D}_M$ represents extrapolated OBM filtrate optical and density properties, as opposed to $D_M$, which was calculated in Equation (7) to represent estimated OBM filtrate optical and density properties. It is noted that the projection above mirrors the form of the projection of Equation (4) and step 310, which was used to obtain extrapolated optical and density properties $\tilde{D}_F$ of the formation fluid. As mentioned previously, in this second scenario of little fluid density contrast between OBM filtrate and formation fluid, substantially the same PCA projection can be utilized to obtain optical and density properties for both the OBM filtrate and the formation fluid. As compared to the first scenario of high fluid density contrast, this second scenario foregoes the real-time optical property measurement and contamination level estimation of Equations (5)-(7) and instead substitutes a second PCA extrapolation/projection operation.

Accordingly, in this second scenario the two PCA extrapolation/projection operations (i.e. of steps 310 and 312) can be performed simultaneously, concurrently, or in some other manner not strictly requiring a successive order between the two steps (as compared to the first scenario of high fluid density contrast, wherein step 310 is a required input to Equation (7) and forces steps 310 and 312 to be performed successively). In some embodiments, a dedicated hardware element such as an ASIC (application-specific integrated circuit) or a discrete processing system/sub-system might be provided to perform PCA extrapolation/projection.

An additional implication of foregoing Equations (5)-(7) when calculating in this second scenario of little fluid density contrast is that it is no longer strictly necessary to estimate the density $\rho_F$ of the formation fluid as given by step 308, as $\rho_F$ is only required as input to Equation (7). However, in some embodiments in can be desirable to still perform step 308, as $\rho_F$ can be used to provide an end member constraint to the formation fluid, or to provide some other constraint, as will be further detailed below with respect to step 314.

Finally, it is further noted that, although obtained via different methods and equations, the extrapolated OBM filtrate optical and density properties $\tilde{D}_M$ obtained from Equation (8)/the low density contrast scenario and the estimated OBM filtrate optical and density properties $D_M$ obtained from Equation (7)/the high density contrast scenario can be used interchangeably in the steps described below.

Step 314—Configure MCR ALS

Using either the estimated OBM filtrate optical and density properties $D_M$ obtained in the high fluid density contrast scenario or using the extrapolated OBM filtrate optical and density properties $\tilde{D}_M$ obtained in the low fluid density contrast scenario, a multivariate curve resolution alternating least squares (MCR ALS) technique is applied. The OBM filtrate optical and density properties ($D_M$ or $\tilde{D}_M$) are taken as an initial input comprising a first end member and the formation fluid optical and density properties $\tilde{D}_F$ are taken as an initial input comprising a second end member. Various constraints can be applied to the MCR ALS, including a non-negativity constraint (i.e. it is physically impossible for the OBM contamination percentage to ne negative) and a two end-member concentration closure constraint (in a system with only two end members, an increase in the first end member concentration produces a corresponding decrease in the second end member concentration). Such constraints act to limit the calculation space of the MCR ALS and furthermore, to increase its efficiency, human readability, conformance to reality, etc.

In addition to the non-negativity and two end-member concentration closure, one or more shape constraints can be applied to the concentration profile curves. For example, shape constraints could comprise a requirement that one or more of upper OBM filtrate contamination bound 904 and lower OBM filtrate contamination bound 902 to monotonically decrease, exponentially decrease, sufficiently decrease by a certain rate or amount, decrease with a complementary error, or could comprise various other shape constraints that would be appreciated by one of ordinary skill in the art.

And end member constraint can also be utilized such that a concentration profile must take certain values at a given end member. For example, drilling fluid is known to contain zero methane and to generally contain zero asphaltenes. These two known compositional factors can be configured as end member constraints that can be applied to a drilling fluid concentration profile. It is also possible to apply end member constraints to the formation fluid end member. For example, such end member constraints might include a density value determined by a pressure test gradient (or using the formation fluid density $\rho_F$ as determined in step 308 from Equation (4)).

A multi-depth constraint might be utilized, wherein an example pump-out is divided into five different zones, each zone having its own concentration profile, and wherein the OBM filtrates for each different zone/zone concentration profile all must have the same fingerprint or characteristics, regardless of their depth. In this manner, the continuity of the OBM filtrate is enforced, whereas in the absence of a multi-depth constraint, the OBM filtrates for concentration profiles calculated at different zones/depths would not necessarily have any consistency or relationship.

A thermodynamic constraint could be utilized, such that one or more end members are required to follow a thermodynamic end-member basis function and/or such that general fluid properties must follow a specified thermodynamic model as well. Such thermodynamic models include, but are not limited to, a cubic equation of state, an SRK (Soave-Redlich-Kwong) cubic equation of state, a Peng-Robinson equation of state, etc.

Finally, while specific reference is made herein to an MCR ALS calculation, it is appreciated that the present disclosure is not necessarily limited to an MCR ALS alone and can include or otherwise encompass further multivariate processing techniques such as trilinear decomposition and other such three-way resolution procedures.

Figure 9:
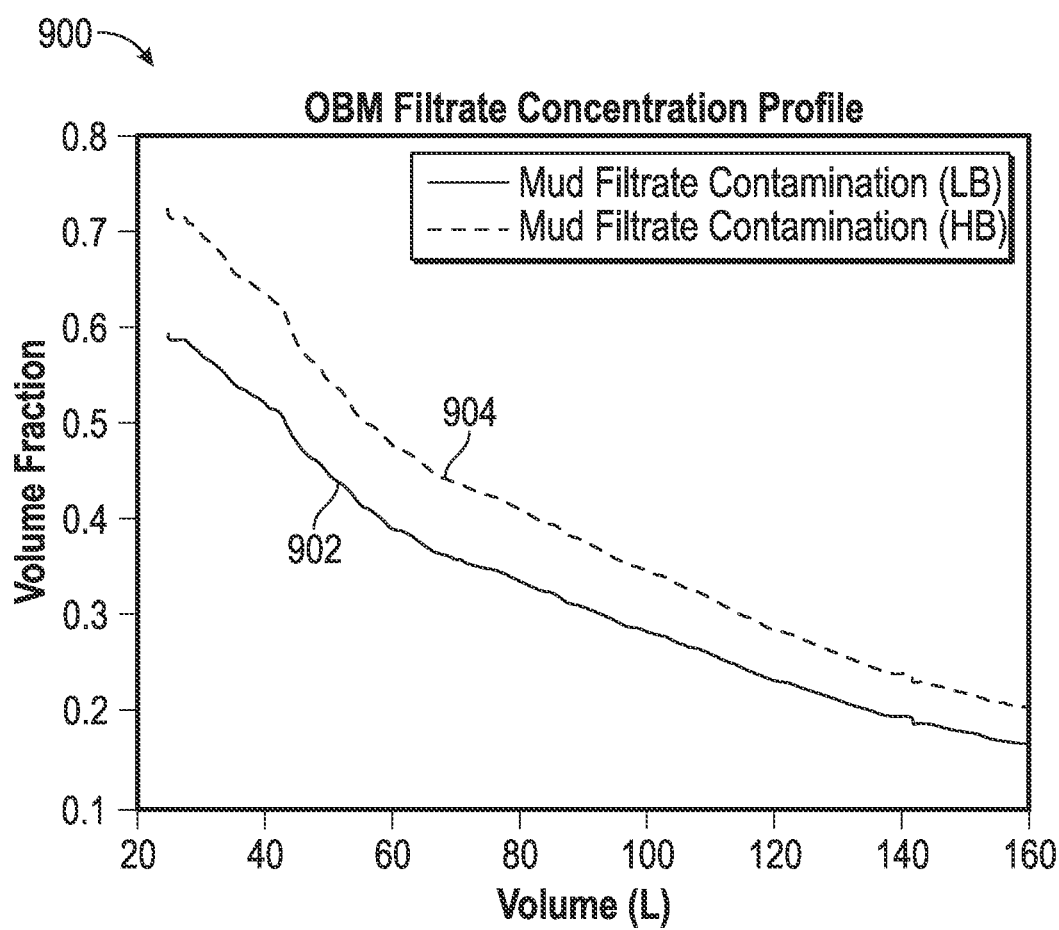
FIG. 9 is an exemplary concentration profile produced by a method of the present disclosure.

Step 316—Generate OBM Filtrate and Formation Fluid Concentration Profiles Using the MCR ALS After appropriate constraints have been selected and applied in step 314, the MCR ALS generates concentration profiles of the two end-members (i.e. OBM filtrate and formation fluid) and their corresponding optical and density properties. With respect to the contamination prediction that is an object of the present disclosure, the concentration profile $P_F$ of the OBM filtrate provides a final estimation of OBM filtrate contamination during the cleanup process:

$$P_F = P \cdot K + E \quad (9)$$

where P represents the concentration profiles of the two end members, K represents the spectral and density profiles of the two end members, and E is a residual error value. One such example concentration profile (alternately referred to herein as a contamination profile) $P_F$ is depicted graphically in FIG. 9 as OBM filtrate concentration profile 900. Contamination profile 900 comprises an OBM filtrate contamination lower bound 902 and an OBM filtrate contamination upper bound 904 which act to collectively define a compositional percentage or volume fraction of OBM filtrate vs. formation fluid. In some embodiments, this percentage can be defined as a function of the pumped out volume during the cleanup process. As would be expected, the OBM filtrate percentage (i.e. the contamination level) drops in response to an increasing volume being pumped out of the well during the cleanup process.

Because various sources of error may be introduced in one or more of the measurements and/or calculations disclosed above, and due to the fact that many of the calculations above are estimations or extrapolations, the contamination profile $P_F$ is characterized by some inherent ambiguity. This ambiguity is captured by the vertical distance between the upper and lower OBM filtrate contamination bounds 904 and 902. In some instances, it can be desirable to reduce this ambiguity to within a certain level, which is often specific to the operational/formation parameters and/or to the analytical goals of the downhole fluid sampling to which the disclosed contamination prediction is applied. In general, the application of further constraints can be effective in accomplishing this goal, at the cost of further computational time and power.

In instances where multiple signals are being analyzed, only some signals or may be constrained, while others could remain unconstrained. In some embodiments, it might be desirable to apply multiple constraints to a single signal.

Step 318—Post-Process OBM Filtrate Contamination Profile

The contamination profile $P_F$ (900 in FIG. 9) provides a volume fraction measurement of OBM filtrate contamination. In a first post-processing technique, it can be desirable to convert concentration profile 900 such that it indicates OBM filtrate contamination by mass. This conversion can be achieved by using density information of the OBM filtrate, as mass is a product of volume and density.

From concentration profile 900, whether indicated as a volume or mass fraction measurement, the originally obtained downhole signals (i.e. the optical data obtained from one or more sensor channels on a logging tool and the density data obtained from one or more other sensor channels on the logging tool) can be modified in order to permit a more accurate analysis of the downhole sample to which the downhole signals correspond. More particularly, the contamination profile $P_F$ can be utilized to generate a plurality of fluid sample signals from the plurality of downhole signals, such that in each fluid sample signal the contribution of the OBM filtrate has been suppressed, masked, attenuated, or removed. For example, a filter could be automatically constructed based on one or more input parameters that are derived or extracted from the specific contamination profile $P_F$ that is determined for a given downhole sample in accordance with the method described above. The construction (and application) of such a filter can comprise an additional post-processing step or can be a part of post-processing step 318. In some embodiments, this process could be repeated in order to suppress the effect or contribution of multiple other contaminants that may be present in the downhole sample in addition to OBM filtrate. From the plurality of fluid sample signals, a fluid analysis of the downhole sample can subsequently be performed in a more efficient manner and with a much greater accuracy, as there will be substantially less uncertainty in the results of this fluid analysis as compared to a conventional fluid analysis that has not been compensated for contamination.

In some embodiments, one or more compositional measurements of methane (C1), Asphaltenes, gas-to-oil ratio (GOR), and other such measurements that may also be derived from a regression analysis of optical data, can replace density as an estimated parameter in the presently disclosed multivariate contamination analysis.

In some embodiments, temperature and/or pressure sensor data can also be fused with the optical and density data of step 306, thereby providing additional or alternate multivariate datasets for the presently disclosed multivariate contamination prediction analysis. If temperature and pressure data are included with the previously disclosed optical and density data, then the MCR ALS analysis of steps 314 and 316 can be defined as a four component mixing problem rather than a two component mixing problem. In this case, the four components are the OBM filtrate, the formation fluid, a temperature pseudo-component, and a pressure pseudo-component. Conceptually, the temperature and pressure pseudo-components can be understood as functioning to account for variations in optical and density signals that are not related to fluid composition, i.e. are instead induced by temperature and pressure fluctuations. In this manner, the desired optical and density properties, as well as the subsequent contamination prediction analysis, can be better achieved.

After the MCR decomposition of step 316 and Equation (9), the optical and density properties of both the temperature and pressure pseudo-components can be obtained. These properties can provide various useful insights to the contamination prediction analysis. For example, the density property of the temperature pseudo-component can be interpreted as a fluid thermal expansion coefficient, as it reflects the density variation induced by temperature change. The density property of the pressure pseudo-component can be interpreted as a fluid compressibility, as it reflects the density variation induced by pressure change.

Statements of the Disclosure Include:

Statement 1: A method for contamination estimation, the method comprising: measuring a downhole sample having a formation fluid and a filtrate to obtain a plurality of downhole signals; conditioning one or more of the plurality of downhole signals to generate one or more conditioned signals; fusing at least two of the conditioned signals to generate a fused multivariate dataset; performing a principle component analysis (PCA) on the fused multivariate dataset to determine optical and density properties of the formation fluid; determining, based on at least the PCA, optical and density properties of the filtrate; and performing a multivariate calculation, based on at least the optical and density properties of the formation fluid and the optical and density properties of the filtrate, to generate concentration profiles of the formation fluid and the filtrate.

Statement 2: The method of statement 1, wherein: the plurality of downhole signals comprises optical transmission data and density data and conditioning the downhole signals comprises smoothing one or more of the optical transmission data and the density data.

Statement 3: The method of statement 2, further comprising transforming smoothed optical transmission data into optical absorbance data by applying a logarithm transform.

Statement 4: The method of statement 1, wherein performing the PCA comprises: calculating PCA scores and a PCA loading space corresponding to the fused multivariate dataset; determining one or more exponential decay best-fit curves for the calculated PCA scores; generating, based on the one or more exponential decay best-fit curves, a formation fluid PCA score estimate; and projecting the formation fluid PCA score estimate into the PCA loading space in order to determine optical and density properties of the formation fluid.

Statement 5: The method of statement 4, wherein determining optical and density properties of the filtrate based on at least the PCA comprises: calculating upper and lower boundaries on a filtrate contamination level; generating, based at least in part on the calculated upper and lower boundaries, a density-based filtrate contamination level; and determining optical and density properties of the filtrate based on at least the density-based filtrate contamination level, the optical and density properties of the formation fluid, and a real-time downhole optical measurement.

Statement 6: The method of statement 4, determining optical and density properties of the filtrate based on at least the PCA comprises: extrapolating one or more of the exponential decay best-fit curves for the calculated PCA scores to one or more early pump-out times; determining, based on the extrapolation, upper and lower boundaries for filtrate PCA scores; generating, based on at least the upper and lower boundaries, a filtrate PCA score extrapolation; and projecting the filtrate PCA score extrapolation into the PCA loading space in order to determine optical and density properties of the filtrate.

Statement 7: The method of statement 1, further comprising disposing a logging tool within a wellbore and obtaining one or more of the plurality of downhole signals with the logging tool.

Statement 8: The method of statement 7, wherein the one or more downhole signals comprise optical transmission data measured from at least a first sensor channel of the downhole tool and density data measured from at least a second sensor channel of the downhole tool.

Statement 9: The method of statement 1, wherein the multivariate calculation comprises a multivariate curve resolution alternating least squares (MCR ALS) calculation or a trilinear decomposition.

Statement 10: The method of statement 9, wherein: the optical and density properties of the formation fluid comprise a first end member initial input to the multivariate calculation; the optical and density properties of the filtrate comprise a second end member initial input to the multivariate calculation; and the multivariate calculation is configured with one or more of non-negativity constraints, end-member concentration closure constraints, shape constraints, end-member constraints, multi-depth constraints, and thermodynamic constraints.

Statement 11: The method of statement 1, wherein: the filtrate is an oil-based mud (OBM) filtrate; and the fused multivariate dataset includes two or more of density data, optical data, temperature data, and pressure data.

Statement 12: The method of statement 11, further comprising: calculating optical and density properties of a temperature pseudo-component derived from the temperature data and calculating optical and density properties of a pressure pseudo-component derived from the pressure data; and calculating, based on at least the optical and density properties of the temperature pseudo-component and the pressure pseudo-component, a fluid compressibility and a fluid thermal expansion coefficient.

Statement 13: The method of statement 1, further comprising: generating a plurality of fluid sample signals from the plurality of downhole signals, the generating based on at least the concentration profiles of the formation and the fluid such that a contribution from the filtrate is attenuated; and performing a fluid analysis of the downhole sample based on the plurality of fluid sample signals.

Statement 14: A system comprising: a downhole toll having a sensor array providing two or more sensor channels, the downhole tool configured to acquire a plurality of downhole signals measured from a downhole sample comprising at least a formation fluid and a filtrate; at least one processor in communication with the downhole tool, wherein the processor is coupled with a non-transitory computer-readable storage medium having stored therein instructions which, when executed by the at least one processor, cause the at least one processor to: condition one or more of a plurality of downhole signals measured from the two or more sensor channels of the downhole tool to generate one or more conditioned signals; fuse at least two of the conditioned signals to generate a fused multivariate dataset; perform a principle component analysis (PCA) on the fused multivariate dataset to determine optical and density properties of the formation fluid; determine, based on at least the PCA, optical and density properties of the filtrate; and perform a multivariate calculation, based on at least the optical and density properties of the formation fluid and the optical and density properties of the filtrate, to generate concentration profiles of the formation fluid and the filtrate.

Statement 15: The system of statement 14, wherein the plurality of downhole signals comprises optical transmission data measured from at least a first sensor channel of the downhole tool and density data measured from at least a second sensor channel of the downhole tool and wherein the instructions further cause the at least one processor to condition the downhole signals by: smoothing one or more of the optical transmission data and the density data; and transforming optical transmission data into optical absorbance data by applying a logarithm transform.

Statement 16: The system of statement 14, wherein the instructions further cause the at least one processor to perform the PCA by: calculating PCA scores and a PCA loading space corresponding to the fused multivariate dataset; determining one or more exponential decay best-fit curves for the calculated PCA scores; generating, based on the one or more exponential decay best-fit curves, a formation fluid PCA score estimate; and projecting the formation fluid PCA score estimate into the PCA loading space in order to determine optical and density properties of the formation fluid.

Statement 17: The system of statement 16, wherein the instructions further cause the at least one processor to determine optical and density properties of the filtrate based on at least the PCA by: calculating upper and lower boundaries on a filtrate contamination level; generating, based at least in part on the calculated upper and lower boundaries, a density-based filtrate contamination level; and determining optical and density properties of the filtrate based on at least the density-based filtrate contamination level, the optical and density properties of the formation fluid, and a real-time downhole optical measurement.

Statement 18: The system of statement 16, wherein the instructions further cause the at least one processor to determine optical and density properties of the filtrate based on at least the PCA by: extrapolating one or more of the exponential decay best-fit curves for the calculated PCA scores to one or more early pump-out times; determining, based on the extrapolation, upper and lower boundaries for filtrate PCA scores; generating, based on at least the upper and lower boundaries, a filtrate PCA score extrapolation; and projecting the filtrate PCA score extrapolation into the PCA loading space in order to determine optical and density properties of the filtrate.

Statement 19: The system of statement 14, wherein the multivariate calculation comprises a multivariate curve resolution alternating least squares (MCR ALS) calculation or a trilinear decomposition.

Statement 20: The system of statement 19, wherein: the optical and density properties of the formation fluid comprise a first end member initial input to the multivariate calculation; the optical and density properties of the filtrate comprise a second end member initial input to the multivariate calculation; and the multivariate calculation is configured with one or more of non-negativity constraints, end-member concentration closure constraints, shape constraints, end-member constraints, multi-depth constraints, and thermodynamic constraints.

Statement 21: The system of statement 14, wherein: the filtrate is an oil-based mud (OBM) filtrate and the fused multivariate dataset includes two or more of density data, optical data, temperature data, and pressure data.

Statement 22: The system of statement 21, wherein the instructions further cause the at least one processor to: calculate optical and density properties of a temperature pseudo-component derived from the temperature data; calculate optical and density properties of a pressure pseudo-component derived from the pressure data; and calculate, based on at least the optical and density properties of the temperature pseudo-component and the pressure pseudo-component, a fluid compressibility and a fluid thermal expansion coefficient.

Statement 23: The system of statement 14, wherein the instructions further cause the at least one processor to: generate a plurality of fluid sample signals from the plurality of downhole signals, the generating based on at least the concentration profiles of the formation and the fluid such that a contribution from the filtrate is attenuated; and perform a fluid analysis of the downhole sample based on the plurality of fluid sample signals.

What is claimed is:

1. A method for estimation of properties of formation fluid and filtrate, the method comprising:
measuring, by a downhole tool having a sensor array providing two or more sensor channels, a downhole sample having a formation fluid and/or a filtrate to obtain a plurality of downhole signals;
conditioning, by a processor in communication with the downhole tool, one or more of the plurality of downhole signals to generate one or more conditioned signals;
fusing, by the processor, at least two of the conditioned signals to generate a fused multivariate dataset; and
performing, by the processor, a multivariate calculation, based on at least the fused multivariate dataset, to estimate properties of the formation fluid and/or the filtrate.

2. The method of claim 1, wherein:
the plurality of downhole signals comprises optical transmission data and density data; and conditioning the downhole signals comprises smoothing one or more of the optical transmission data and the density data.

3. The method of claim 2, further comprising transforming smoothed optical transmission data into optical absorbance data by applying a logarithm transform.

4. The method of claim 1, wherein the properties of the formation fluid and/or the filtrate include at least one of the following: optical properties, density, temperature, pressure, composition, and pseudo components more compositional measurements of methane (C1), Asphaltenes, and/or gas-to-oil ratio (GOR).

5. The method of claim 1, further comprising:
disposing a logging tool within a wellbore; and
obtaining the downhole sample with the logging tool.

6. The method of claim 5, wherein the one or more downhole signals comprise optical transmission data measured from at least a first sensor channel of the downhole tool and density data measured from at least a second sensor channel of the downhole tool.

7. The method of claim 1, wherein the multivariate calculation comprises a multivariate curve resolution alternating least squares (MCR ALS) calculation or a trilinear decomposition.

8. The method of claim 7, wherein:
the multivariate calculation is configured with one or more of non-negativity constraints, end-member concentration closure constraints, shape constraints, end-member constraints, multi-depth constraints, and thermodynamic constraints.

9. The method of claim 1, wherein:
the filtrate is an oil-based mud (OBM) filtrate; and
the fused multivariate dataset includes two or more of density data, optical data, temperature data, and pressure data.

10. The method of claim 9, further comprising:
calculating optical and density properties of a temperature pseudo-component derived from the temperature data;
calculating optical and density properties of a pressure pseudo-component derived from the pressure data; and
calculating, based on at least the optical and density properties of the temperature pseudo-component and the optical and density properties of the pressure pseudo-component, a fluid compressibility and a fluid thermal expansion coefficient.

11. The method of claim 1, further comprising:
generating a plurality of fluid sample signals from the plurality of downhole signals, the generating based on at least a concentration profile of the formation fluid and/or the filtrate such that a contribution from the filtrate is attenuated; and
performing a fluid analysis of the downhole sample based on the plurality of fluid sample signals.

12. The method of claim 1, wherein the multivariate calculation is based on at least optical and density properties of the formation fluid and/or optical and density properties of the filtrate.

13. A system comprising:
a downhole tool having a sensor array providing two or more sensor channels, the downhole tool configured to acquire a plurality of downhole signals measured from a downhole sample, the downhole sample comprising at least a formation fluid and/or a filtrate; and at least one processor in communication with the downhole tool, wherein the processor is coupled with a non-transitory computer-readable storage medium having stored therein instructions which, when executed by the at least one processor, cause the at least one processor to:

condition one or more of the plurality of downhole signals measured from the two or more sensor channels of the downhole tool to generate one or more conditioned signals;

fuse at least two of the conditioned signals to generate a fused multivariate dataset; and perform a multivariate calculation, based on at least the fused multivariate dataset, to estimate properties of the formation fluid and/or the filtrate.

14. The system of claim 13, wherein the plurality of downhole signals comprises optical transmission data measured from at least a first sensor channel of the downhole tool and density data measured from at least a second sensor channel of the downhole tool and wherein the instructions further cause the at least one processor to condition the downhole signals by:

smoothing one or more of the optical transmission data and the density data; and transforming optical transmission data into optical absorbance data by applying a logarithm transform.

15. The system of claim 13, wherein the properties of the formation fluid and/or the filtrate include at least one of the following: optical properties, density, temperature, pressure, composition, and pseudo components more compositional measurements of methane (C1), Asphaltenes, and/or gas-to-oil ratio (GOR).

16. The system of claim 13, wherein the multivariate calculation comprises a multivariate curve resolution alternating least squares (MCR ALS) calculation or a trilinear decomposition.

17. The system of claim 16, wherein:
the multivariate calculation is configured with one or more of non-negativity constraints, end-member concentration closure constraints, shape constraints, end-member constraints, multi-depth constraints, and thermodynamic constraints.

18. The system of claim 13, wherein:
the filtrate is an oil-based mud (OBM) filtrate; and
the fused multivariate dataset includes two or more of density data, optical data, temperature data, and pressure data.

19. The system of claim 18, wherein the instructions further cause the at least one processor to:
calculate optical and density properties of a temperature pseudo-component derived from the temperature data;
calculate optical and density properties of a pressure pseudo-component derived from the pressure data; and
calculate, based on at least the optical and density properties of the temperature pseudo-component and the optical and density properties of the pressure pseudo-component, a fluid compressibility and a fluid thermal expansion coefficient.

20. The system of claim 13, wherein the instructions further cause the at least one processor to:
generate a plurality of fluid sample signals from the plurality of downhole signals, the generating based on at least a concentration profile of the formation fluid and/or the filtrate such that a contribution from the filtrate is attenuated; and
perform a fluid analysis of the downhole sample based on the plurality of fluid sample signals.

21. The system of claim 13, wherein the multivariate calculation is based on at least optical and density properties of the formation fluid and/or optical and density properties of the filtrate.

* * * * *